(12) United States Patent
Horvath et al.

(10) Patent No.: US 9,328,108 B2
(45) Date of Patent: *May 3, 2016

(54) PROCESS FOR PREPARING AN INTERMEDIATE OF THE MACROCYCLIC PROTEASE INHIBITOR TMC 435

(71) Applicant: Janssen Pharmaceuticals, Inc., Titusville, NJ (US)

(72) Inventors: Andras Horvath, Turnhout (BE); Stijn Wuyts, Oostham (BE); Dominique Paul Michel Depré, Hamme-Mille (BE); Wouter Louis J. Couck, Zomergem (BE); Jozef Ludo Jan Cuypers, Vossellar (BE); Syuzanna Harutyunyan, Groningen (NL); Gregory Fabien Sebastian Binot, Monthey (CH)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,770

(22) Filed: Feb. 9, 2015

(65) Prior Publication Data

US 2015/0152098 A1    Jun. 4, 2015

Related U.S. Application Data

(63) Continuation of application No. 14/350,138, filed as application No. PCT/IB2012/055900 on Oct. 26, 2012, now Pat. No. 8,981,082.

(30) Foreign Application Priority Data

Oct. 28, 2011  (EP) .................................... 11187025

(51) Int. Cl.
  *C07D 471/04*    (2006.01)
  *C07D 417/14*    (2006.01)
  *C07D 417/04*    (2006.01)

(52) U.S. Cl.
  CPC ............ *C07D 417/14* (2013.01); *C07D 417/04* (2013.01)

(58) Field of Classification Search
  CPC ....................................................... C07D 471/04
  See application file for complete search history.

(56) References Cited

FOREIGN PATENT DOCUMENTS

| | | |
|---|---|---|
| CN | 1771257 A | 5/2006 |
| WO | WO 2004/089974 A1 | 10/2004 |
| WO | WO 2007/014926 | 2/2007 |
| WO | WO 2007/030656 | 3/2007 |
| WO | WO 2009/073780 | 6/2009 |
| WO | WO 2010/015545 | 2/2010 |
| WO | 2010/072742 A1 | 7/2010 |

OTHER PUBLICATIONS

Goldring et al., "Synthesis of Macrocyclic Lactams and Lactones via Ring-Closing Olefin Metathesis", Tetrahedron Letters, 39, pp. 4955-4958 (1998).
Xiongsheng Yao, "Olefin Metathesis—A New Highly Efficient and Green Method for Organic Synthesis", Applied Science and Technology, vol. 17, No. 10, pp. 24-27, May 21, 2009.
English Translation of Search Report for Taiwan App No. 101139616 dated Feb. 15, 2016.
Snider et al., "Total Synthesis of (±)-Martinellic Acid", Organic Letters, vol. 3, No. 26, pp. 4217-4220 (2001).

*Primary Examiner* — Bruck Kifle
(74) *Attorney, Agent, or Firm* — Andrea Jo Kamage

(57) ABSTRACT

The present invention relates to an improved process for preparing (2R,3aR,10Z,11aS,12aR,14aR)-cyclopenta[c]cyclopropa[g][1,6]diazacyclotetradecine-12a(1H)-carboxylic acid, 2,3,3a,4,5,6,7,8,9,11a,12,13,14,14a-tetradecahydro-2-[[7-methoxy-8-methyl-2-[4-(1-methylethyl)-2-thiazolyl]-4-quinolinyl]oxy]-5-methyl-4,14-dioxo-, ethyl ester. This compound is an intermediate in the overall synthesis route of the macrocyclic compound TMC 435. TMC 435 is an inhibitor of NS3/4A protease which plays an important role in the replication of the hepatitis C virus.

11 Claims, 1 Drawing Sheet conversion of diethyldiallylmalonate (DEDAM) by M2 catalyst in the presence and absence of tetrabutylammonium iodide (TBAI)
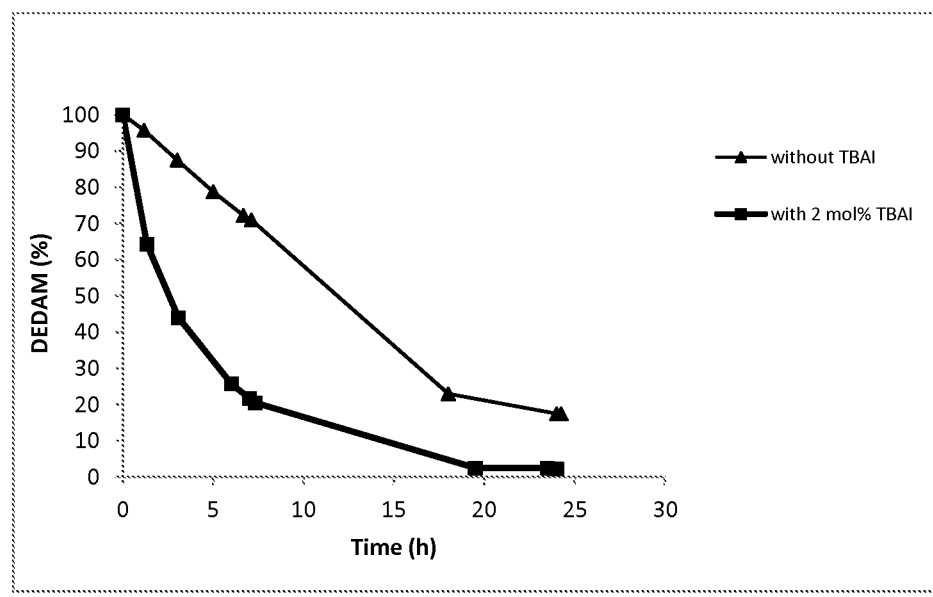

PROCESS FOR PREPARING AN INTERMEDIATE OF THE MACROCYCLIC PROTEASE INHIBITOR TMC 435

CROSS-REFERENCE TO RELATED APPLICATIONS

This application is a continuation application of U.S. application Ser. No. 14/350,138, filed Mar. 19, 2009, currently allowed, which claims the benefit of International Application Number PCT/IB2012/055900, filed 26 Oct. 2012, which claims the benefit of Application Number EP11187025.9, filed 28 Oct. 2011. The entire contents of each of the aforesaid applications are incorporated herein by reference in their entirety.

FIELD OF THE INVENTION

The present invention relates to an improved process for preparing (2R,3aR,10Z,11aS,12aR,14aR)-cyclopenta[c]cyclopropa[g][1,6]diazacyclotetradecine-12a(1H)-carboxylic acid, 2,3,3a,4,5,6,7,8,9,11a,12,13,14,14a-tetradecahydro-2-[[7-methoxy-8-methyl-2-[4-(1-methylethyl)-2-thiazolyl]-4-quinolinyl]oxy]-5-methyl-4,14-dioxo-, ethyl ester (or compound (2) as referred to hereinafter). This compound is an intermediate in the overall synthesis route of the macrocyclic compound TMC 435. TMC 435 is an inhibitor of NS3/4A protease which plays an important role in the replication of the hepatitis C virus.

BACKGROUND OF THE INVENTION

The hepatitis C virus (HCV) is the leading cause of chronic hepatitis, which can progress to liver fibrosis leading to cirrhosis, end stage liver disease, and HCC (hepatocellular carcinoma), making it the leading cause of liver transplantations. Anti-HCV therapy, based on (pegylated) interferon-alpha (IFN-α) in combination with ribavirin, suffers from limited efficacy, significant side effects, and is poorly tolerated in many patients. This prompted the search for more effective, convenient and better-tolerated therapy. Recently, certain protease inhibitors have been approved for use in combination with peginterferon plus ribavirin. However, there is a need for improved protease inhibitors.

WO-2007/014926 describes macrocyclic cyclopentane and proline derivatives including the compound TMC-435 with the structure represented hereafter.

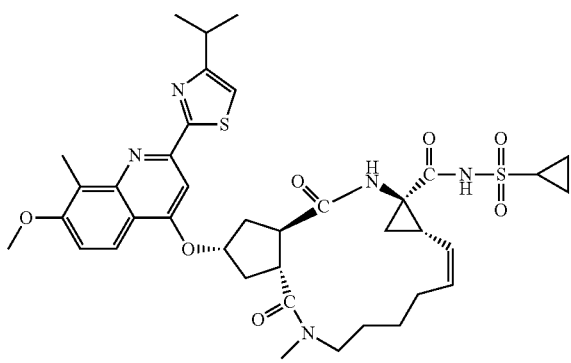

TMC-435

TMC-435 is a very effective inhibitor of the HCV NS3 protease and is particularly attractive in terms of pharmacokinetics. Due to its favorable properties it is being developed as an anti-HCV drug. Consequently there is a need for producing larger quantities of this active ingredient based on processes that provide the product in high yield and with a high degree of purity.

Synthesis procedures to prepare TMC-435 have been disclosed in WO-2007/014926 wherein TMC-435 is identified as compound (47) in Example 5 on page 76.

An important step in the synthesis of TMC-435 as described in WO-2007/014926 is the ring-closing metathesis (RCM) which is depicted below:

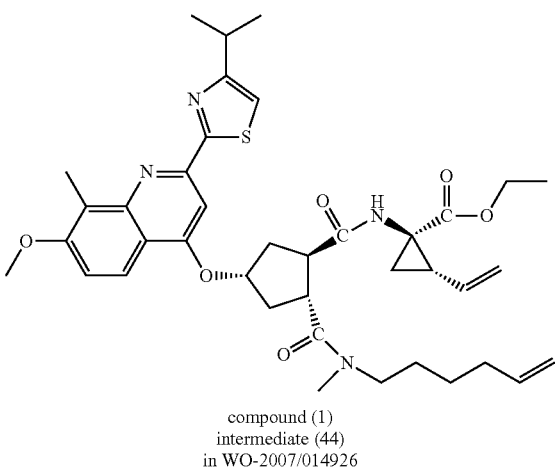

compound (1)
intermediate (44)
in WO-2007/014926

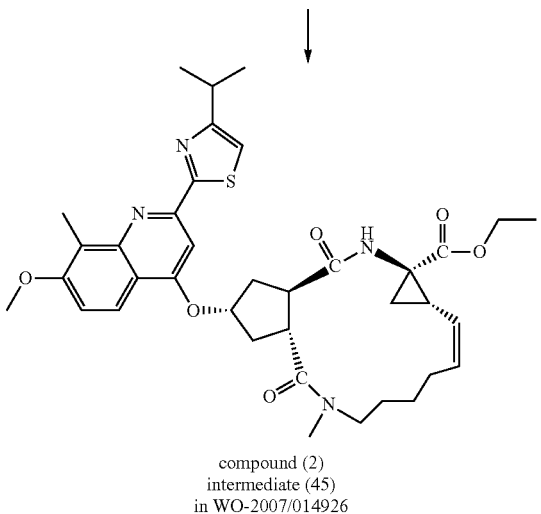

compound (2)
intermediate (45)
in WO-2007/014926

Said ring-closing metathesis has been described in WO-2007/014926 in Example 4 Step E on page 74. Ring-closing metathesis of intermediate (44) in WO-2007/014926 is done by means of a Hoveyda-Grubbs first-generation catalyst in 1,2-dichloroethane at 75° C. for 12 hours resulting in intermediate (45) with a 60% yield. Large amounts of oligomeric byproducts are formed under these conditions, and tedious purification procedures, e.g. preparative chromatography, are required to isolate the product from the reaction mixture.

The efficiency by which the ring-closing metathesis cyclization occurs is important because the starting material, i.e. compound (1) or intermediate (44) in WO-2007/014926, is the result of a long multi-step process. The ring-closing metathesis reaction produces side products such as dimers and polymers thereby lowering the yield and complicating product isolation. One solution that has been proposed in Goldring et al., Tetrahedron Letters 39, 4955-4958 (1998), is the introduction of a N-protective group, in particular a Boc group, on the secondary amide function which is removed after the ring-closing metathesis. Said introduction and removal of a N-protective group to increase the yield of ring-closing metathesis in the synthesis of macrocyclic compounds has also been described in WO-2007/030656, WO-2009/073780 and WO-2010/015545. The N-protective group described in said references is e.g. $C_{1-6}$alkyloxycarbonyl such as Boc (tert-butyloxycarbonyl), $C_{1-6}$alkylcarbonyl, benzoyl and arylcarbonyl (in particular, the N-protective group is benzoyl).

When applying this N-protective group technology using Boc in the ring-closing metathesis of compound (1) it turned out that the Boc-group could only be removed from the macrocyclic metathesis product under drastic conditions, in particular prolonged heating with strong acids (e.g. sulfuric acid or benzenesulfonic acid), resulting in product decomposition during the Boc-deprotection process. This procedure is depicted below in Scheme 1.

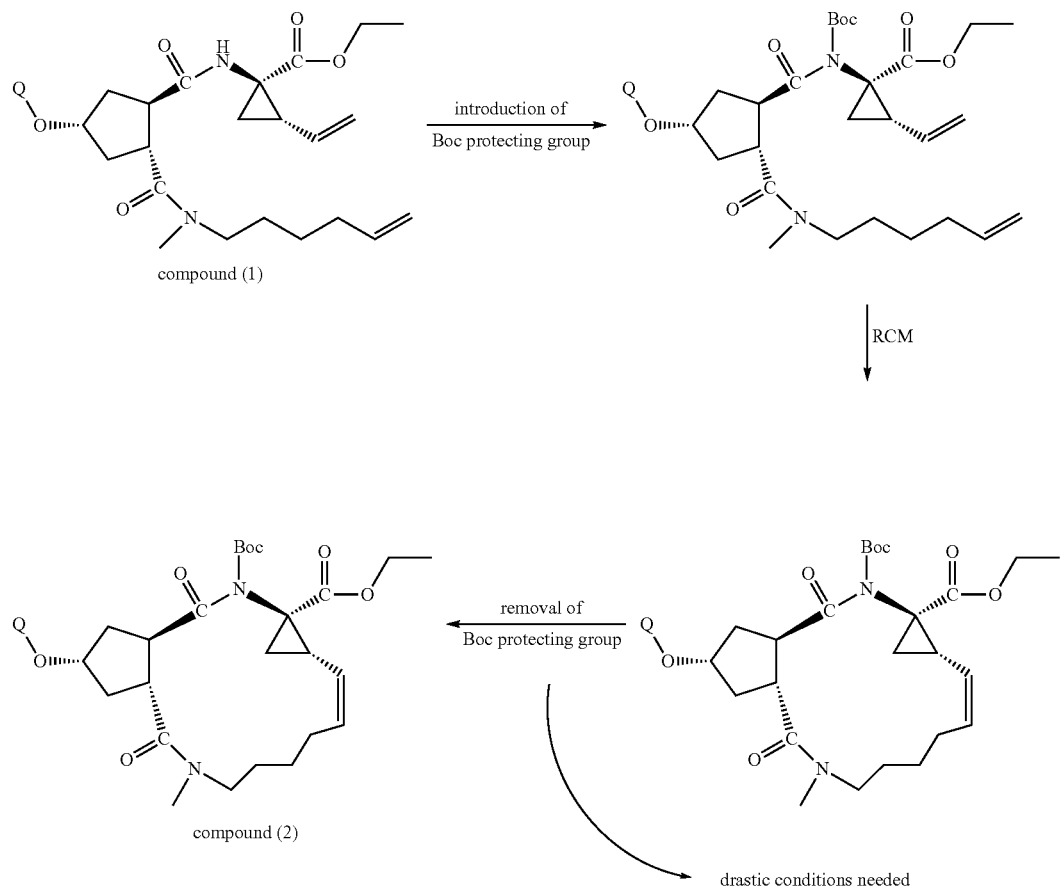

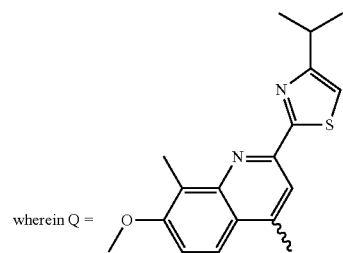

When applying the N-benzoyl protective group, on the other hand, cleavage of the benzoyl protecting group can be done by treatment of the N-benzoylated macrocycle with bases such as KOH. This cleavage is also accompanied by product loss due to non-selective attack of the base and ring opening of the macrocyle. Introduction of both the Boc and the benzoyl group needs an additional synthesis step, and a purification is necessary before the ring closing metathesis to avoid catalyst poisoning.

Hence there is a need to improve the efficiency of this ring closing metathesis reaction, preferably with as few additional steps as possible. In particular there is a need for a protecting group on the secondary amide function that can be removed easily under non-drastic reaction conditions.

It now has been found that halogenated acyl groups can be used in situ in the ring-closing metathesis reaction and can be removed easily upon completion of the reaction. It further has been found that the protection-macrocyclization-deprotection cycle can be conducted in a one-pot process in high yield of the end product, which is obtained in high purity.

The process of the invention offers a straightforward, quick and economic procedure to produce compound (2), which can easily converted to the end product TMC-435.

DESCRIPTION OF THE INVENTION

In one aspect, the present invention relates to a process for preparing a compound of formula (II), which is characterized by the steps of
a) acylating a diene compound of formula (I), wherein $R^1$ is $C_{1-6}$alkyl, compound (I)

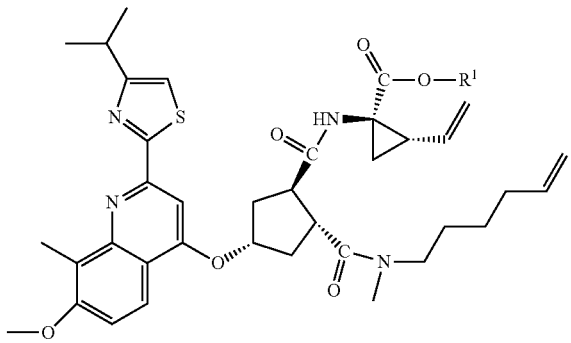

with a halogenated acyl compound $(R^2\text{—CO})_2O$ or $R^2\text{—COCl}$, wherein $R^2$ is polyhalo$C_{1-4}$alkyl, followed by a ring-closing metathesis reaction of the acylated reaction product with a suitable catalyst in a reaction-inert solvent to yield a compound of formula (III); and compound (III)

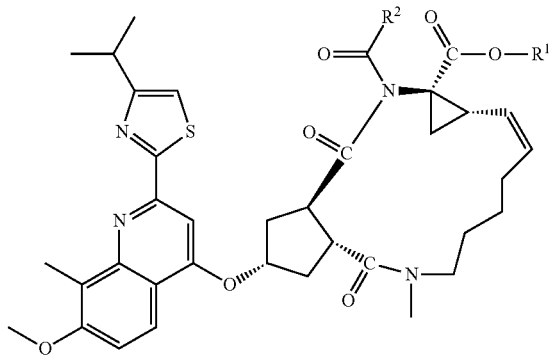

b) removing the halogenated acyl group from compound (III) thus obtaining the compound of formula (II) wherein $R^1$ is $C_{1-6}$alkyl.

compound (II)

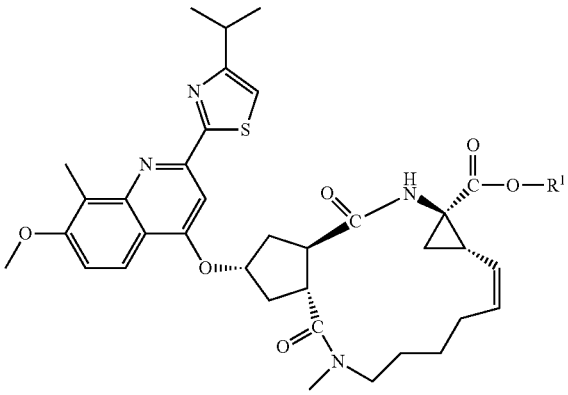

As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;
$C_{1-6}$alkyl is meant to include $C_{1-4}$alkyl and the higher homologues thereof having 5 or 6 carbon atoms, such as, for example, 2-methylbutyl, pentyl, hexyl and the like;
polyhalo$C_{1-4}$alkyl is defined as polyhalosubstituted $C_{1-4}$alkyl, in particular $C_{1-4}$alkyl (as hereinabove defined) substituted with 1 to 6 (e.g. 1 to 4) halogen atoms such as fluoromethyl, difluoromethyl, trifluoromethyl, chloro-difluoromethyl, trifluoroethyl, heptafluoro-propyl and the like. Preferably, such polyhalo$C_{1-4}$alkyl groups are entirely substituted by halo atoms (i.e. there are no hydrogen atoms).

In an embodiment of the present invention the substituent the substituent $R^1$ in the compounds of formula (II) is defined $C_{1-4}$alkyl, in particular ethyl, and $R^2$ in the halogenated acyl compound $(R^2\text{—CO})_2O$ or $R^2\text{—COCl}$ represents polyhalo$C_{1-4}$alkyl in particular trifluoromethyl, chlorodifluoromethyl, heptafluoropropyl, and the like.

It is believed that the acylation reaction performed on compound of formula (I) yields an N-acylated reaction product but it is not excluded that also O-acylation occurs. Likewise, the acyl group in compounds of formula (III) can be attached to the N or to the O atom of the amide functional group.

The ring-closing metathesis in reaction step a) above to obtain compound (III) is done by an olefin ring-closing metathesis reaction in the presence of a suitable metal catalyst such as e.g. an ylidene Ru-based catalyst, in particular an optionally substituted alkylidene or indenylidene catalyst, such as [1,3-bis(2,4,6-trimethylphenyl)-2-imidazolidinylidene]dichloro(phenylmethylene)(tricyclohexylphosphine)ruthenium, (Grubbs 2 catalyst), [1,3-bis(2,4,6-trimethylphenyl)-2-imidazolidinylidene]dichloro[[2-(1-methylethoxy-κO)phenyl]methylene-κC]ruthenium (Hoveyda-Grubbs 2 catalyst) dichloro(3-phenyl-1H-inden-1-ylidene)bis(tricyclohexylphosphine)ruthenium or bis(tricyclohexyl-phosphine) [(phenylthio)methylene]ruthenium dichloride. Other catalysts that can be used are Grubbs first and Hoveyda-Grubbs first generation catalysts, i.e. dichloro(phenylmethylene)bis(tricyclohexylphosphine)ruthenium and dichloro[[2-(1-methylethoxy-α-O)phenyl]methylene-α-C](tricyclohexylphosphine)ruthenium, respectively. Of particular interest are the catalysts[1,3-bis(2,4,6-trimethylphenyl)-2-imidazolidinylidene]dichloro(3-phenyl-1H-inden-1-ylidene) (tricyclohexylphosphine)ruthenium (M2 catalyst), [1,3-bis(2,4,6-trimethylphenyl)-2-imidazolidinylidene] dichloro(3-phenyl-1H-inden-1-ylidene)(triphenylphosphine) ruthenium (M20 catalyst) and [1,3-bis(2,4,6-trimethylphenyl)-2-imidazolidinylidene]dichloro[[4-[(dimethylamino)sulfonyl]-2-(1-methylethoxy-κO)phenyl] methyl-κC]ruthenium (Zhan1b catalyst).

The metathesis reactions can be conducted in a suitable solvent such as for example an ether, e.g. THF, dioxane; halogenated hydrocarbons, e.g. dichoromethane, chloroform, 1,2 dichloroethane and the like, aromatic hydrocarbons, e.g. toluene, or halogenated aromatic hydrocarbons like trifluoromethylbenzene, fluorobenzene, hexafluorobenzene and the like.

The protection step a) whereby the secondary amide function is protected with a $R^2$—CO group by acylating a compound of formula (I) with a halogenated acyl compound $(R^2$—$CO)_2O$ or $R^2$—COCl can be performed using any of the conventional nitrogen-protection protocols and conditions well known in the art. Suitable protection procedures may also be found in the Working Examples section herein.

Removing the halogenated acyl group $R^2$—CO from compound (III) in step b) by deprotection can be performed using any of the conventional nitrogen-deprotection protocols and conditions well known in the art. Suitable deprotection procedures may also be found in the Working Examples section herein, for instance treatment with a secondary amine, e.g. an aqueous dimethylamine solution.

In an embodiment of the present invention, steps a) and b) are executed as a "one pot synthesis" procedure.

The intermediate products that are prepared by the process of the invention need not be isolated (e.g. from the reaction mixture including solvent) or purified, and hence this may reduce the number of process steps that need to be taken. For example the product of process step (a) (the compound of formula (III)) need not be isolated but may be used directly in the subsequent step (b) (where the halogenated acyl group is removed to yield a compound of formula (II)). Similarly, the acylation and metathesis reaction steps may be performed with the need to isolate any intermediate products.

In a further aspect of the invention it has been found that the addition of a reaction solvent soluble tetraalkylammonium iodides such as e.g. tetramethylammonium iodide (TMAI), tetraethylammonium iodide (TEAI), tetrapropylammonium iodide (TPAI) or tetrabutylammonium iodide (TBAI), improves the reaction rate and yield of the ring closing metathesis reaction that is carried out in the presence of a ylidene Ru based catalyst (see Examples 10 to 13). The tetraalkylammonium iodides have to be soluble in the solvent chosen for conducting the ring closing metathesis and for instance in apolar solvents the lower alkyl tetraalkylammonium iodides such as TMAI may not be dissolve completely and a higher alkyl tetraalkylammonium iodides should then be used such as e.g. TBAI.

The present invention also relates to novel compounds of formula (III)

compound (III)

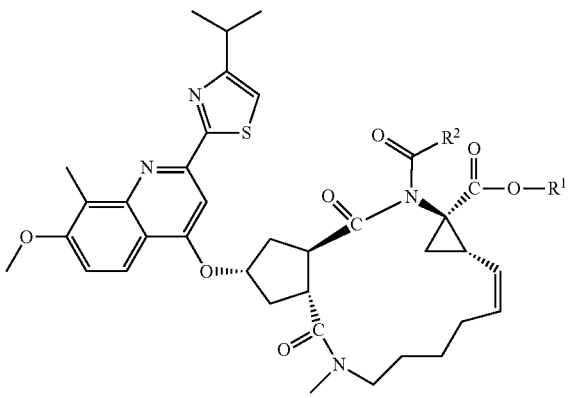

wherein $R^1$ represents $C_{1-6}$alkyl and $R^2$ represents polyhalo$C_{1-4}$alkyl.

A particular group of compounds of formula (III) are those compounds of formula (III) wherein $R^1$ represents ethyl and $R^2$ represents trifluoromethyl, chlorodifluoromethyl, or heptafluoropropyl.

In an embodiment of the present invention the substituent $R^1$ in the compounds of formula (III) are defined as $R^1$ represents $C_{1-4}$alkyl, in particular ethyl.

In a further embodiment, there is provided a step for the conversion of the compound of formula (II) (or other compound that results from the process of the invention) to the final HCV protease inhibitor (e.g. TMC435), which process may involve conversion of the —C(O)OR$^1$ moiety to —C(O)—N(H)SO$_2$-cyclopropyl in accordance with known methods (e.g. by reaction with sulfonamine) The final protease inhibitor may then be converted into a pharmaceutical product in a further process step, for example by contacting the product with a pharmaceutically acceptable carrier, diluent and/or excipient. Hence there is provided a corresponding process for preparing such a medicament (or pharmaceutical composition/formulation).

Although it is preferred that the process of the invention may be carried out on precursors to the HCV protease inhibitor TMC435, it will be understood that this methodology may be used to synthesise any macrocycle where a metathesis reaction is the key step. This is embraced in the invention. For example, particularly, the methodology may be used to synthesise other (e.g. similar) HCV protease inhibitors.

In this respect, there is provided a process as described herein, but wherein the following compounds are prepared:

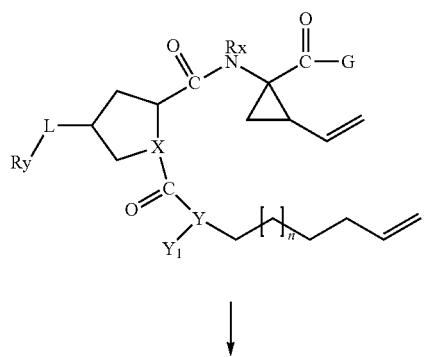

-continued

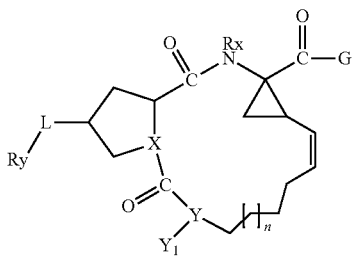

wherein:

n is 0-8 (e.g. 0-6);

$R_x$ represents hydrogen;

G represents $—OR^{x1}$ or $—N(H)SO_2R^{x2}$;

$R^{x1}$ represents hydrogen or $C_{1-6}$ alkyl;

$R^{x2}$ represents $C_{1-6}$ alkyl or $C_{3-6}$ cycloalkyl;

X represents N or CH;

Y represents N or CH;

when Y represents N, then $Y^1$ represents hydrogen or $C_{1-6}$ alkyl;

when Y represents CH, then $Y^1$ represents $—C(O)—R^{x3}$, $—S(O)_{1-2}—R^{x3}$, $—C(S)—R^{x3}$, $—N(R^{x3})—R^{x4}$, $—N(H)—C(O)—O—R^{x3}$ or $—N(H)—C(O)—R^{x4}$;

$R^{x3}$ and $R^{x4}$ independently represent $C_{1-6}$ alkyl, $C_{3-6}$ cycloalkyl, aryl or heteroaryl (which latter two groups are optionally substituted by one or more substituents selected from halo and $C_{1-6}$ alkyl);

more preferably, $R^{x3}$ represents $C_{1-6}$ alkyl or $C_{3-6}$ cycloalkyl (e.g. tert-butyl);

more preferably, $R^{x4}$ represents aryl or heteroaryl, e.g. heteroaryl (e.g. a 5- or 6-membered heteroaryl group containing one to four, e.g. one or two heteroatoms, so forming e.g. pyrimidine (which latter aryl/heteroaryl groups are optionally substituted by one or more substituents selected from halo and $C_{1-6}$ alkyl, e.g. methyl);

L represents —O— or —O—C(O)—;

$R_y$ represents aryl, heteroaryl or cyclic non-aromatic group, all of which are optionally substituted by one or more substituents selected from halo, $C_{1-6}$ alkyl or $R^4$, $R^5$ and $R^6$ (as defined below);

for example $R_y$ may represent the following groups:

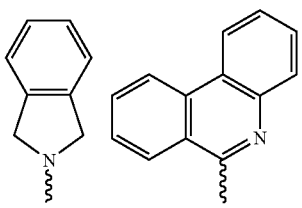

which $R^y$ groups may be substituted as defined herein, e.g. by halo (e.g. fluoro).

Hence, the $R_x$ moiety may be converted from H to $—C(O)R^2$ (as herein defined), followed by metathesis and removal of the $—C(O)R^2$ moiety.

Most preferably, in the above formulae:

$R_y$ represents:

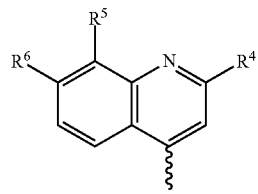

in which:

$R^4$ is selected from the group consisting of phenyl, pyridin-4-yl,

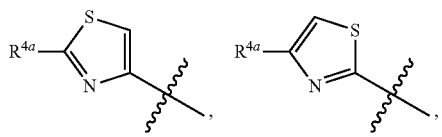

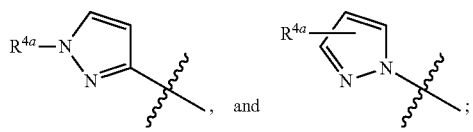

wherein $R^{4a}$ is, each independently, hydrogen, halo, $C_{1-6}$alkyl, amino, or mono- or di-$C_{1-6}$alkylamino;

$R^5$ represents halo, $C_{1-6}$alkyl, hydroxy, $C_{1-6}$alkoxy or polyhalo$C_{1-6}$alkyl (e.g. is methyl, ethyl, isopropyl, tert-butyl, fluoro, chloro, or bromo);

$R^6$ represents $C_{1-6}$alkoxy, mono- or di$C_{1-6}$alkylamino (in particular, $R^6$ represents methoxy);

in particular, $R_y$ represents:

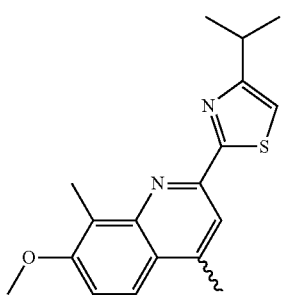

in which the squiggly line on the quinolinyl group represents the point of attachment to the O atoms of the macrocycle (and the precursor thereto).

EXPERIMENTAL PART

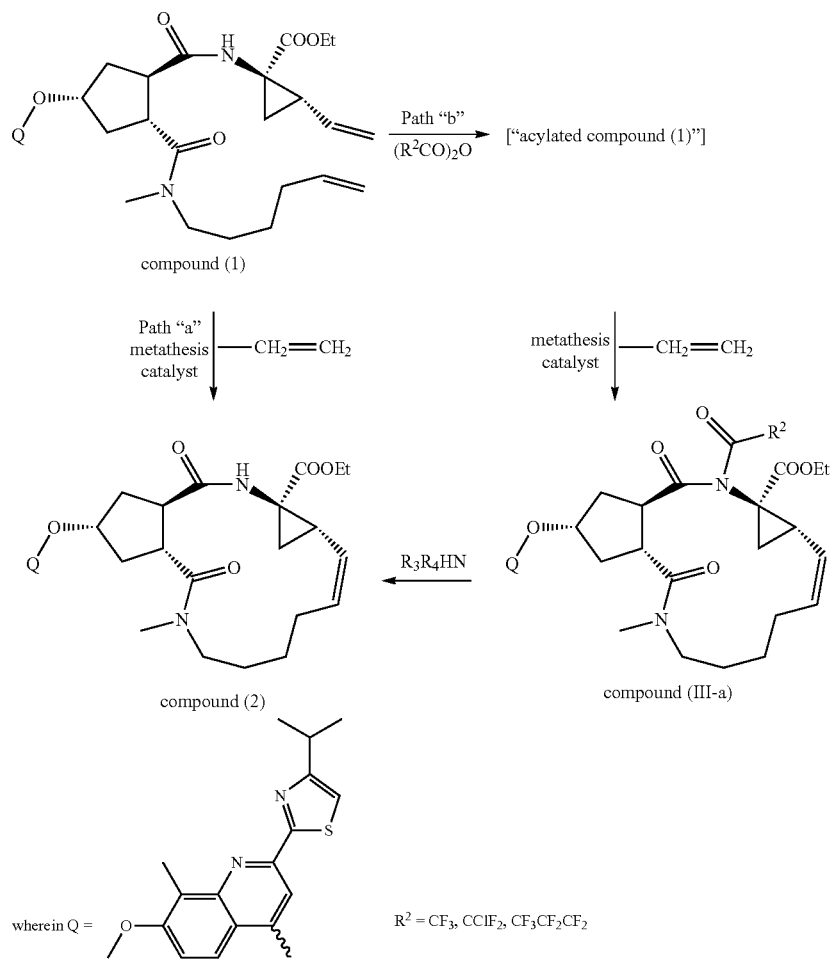

The following reactions (Examples 1-7) were performed in the presence of 5,12-naphthoquinone (NQ), which was used as an internal standard (IS) to determine in situ yields by HPLC analysis. Solutions of the NQ in dichloromethane or in toluene were prepared by mixing 0.206 g of NQ with 100 mL of dichloromethane, or 0.73 g of NQ with 150 mL of toluene, respectively, for 5 minutes, then, optionally, filtering the resulting mixtures. Aliquots of the mixtures of the NQ in dichloromethane or toluene were used in the reactions.

All quantitative analyses described in the experimental part were performed using standard HPLC techniques and using reference materials.

The following analytical method can be used to monitor the reactions described in the working examples below.

| UPLC System | Parameters |
| --- | --- |
| Column: | Acquity UPLC BEH C18 2.1 × 50 mm 1.7 μm |
| Column Temperature: | 35° C. |
| Autosampler Temperature: | Room temperature |
| Flow rate: | 0.6 ml/min |
| Wash solvents: | Weak: water-methanol (90/10, v/v): 600 μl |
|  | Strong: methanol-water (90/10, v/v): 200 μl |

-continued

| UPLC System | Parameters |
| --- | --- |
| Injection volume: | 2.5 μl - Partial loop with needle overfill |
| Detection wavelength: | UV 240 nm |
| Dilution solvent: | DMF |
| Mobile phase A: | 10 mM $NH_4OAc$ in water/acetonitrile (95/5; v/v) |
| Mobile phase B: | Acetonitrile |

| Gradient | Time (min) | % A | % B |
| --- | --- | --- | --- |
| | 0 | 20 | 80 |
| | 2 | 0 | 100 |
| | 2.5 | 0 | 100 |
| | 2.6 | 20 | 80 |
| | 3 | 20 | 80 |

Example 1

Path "a"

1 mL of a solution of NQ in dichloromethane (as prepared above) was added to a solution of 0.17 g (0.24 mmol) of compound (1) in 6 mL of dichloromethane and the resulting solution refluxed with magnetic stirring in a Radley's Caroussel tube for 1 hour. The solution was cooled and a $t_0$ sample was taken to determine initial ratio internal standard (IS) over compound (1). 0.5 mL of a solution of 0.008 g of [1,3-bis(2,4,6-trimethylphenyl)-2-imidazolidinylidene]dichloro(3-phenyl-1H-inden-1-ylidene)(tricyclohexylphosphine)ruthenium (M2 catalyst) in 1 mL of dichloromethane was added and the resulting solution heated to reflux. A sample taken after 3 hours contains 64.8% of unconverted compound (1), 6.5% of the desired compound (2), and 14% of oligomeric species (HPLC area %). After 20 hours reflux, the analysis showed 59% of unconverted compound (1) with 11% of the desired compound (2) formed together with 28% of oligomeric species.

Example 2

Path "b" Wherein $R^2$ is $CF_3$ 1 mL of a solution of NQ in dichloromethane (as prepared above) was added to a solution of 0.17 g (0.24 mmol) of compound (1) in 6 mL of dichloromethane and the resulting solution refluxed with magnetic stirring in a Radley's Caroussel tube for 1 hour. The solution was cooled and a sample was taken to determine initial ratio IS over compound (1). 0.5 mL of trifluoroacetic anhydride $(CF_3CO)_2O$ was added, and the mixture refluxed for 35 minutes. 0.5 mL of a solution of 0.008 g of [1,3-bis(2,4,6-trimethylphenyl)-2-imidazolidinylidene]dichloro(3-phenyl-1H-inden-1-ylidene)(tricyclohexylphosphine) ruthenium (M2 catalyst) in 1 mL of dichloromethane was added and the resulting solution heated to reflux. A sample taken after 3 hours contained 4% of unconverted compound (1), 69% of the desired monomeric macrocycle compound (III-a), wherein $R^2$ is $CF_3$, and 0.8% of "acetylated compound (1)" (HPLC area %). The in situ yield of compound (III-a), wherein $R^2$ is $CF_3$, determined based on the IS, was 65%.

compound (III-a)

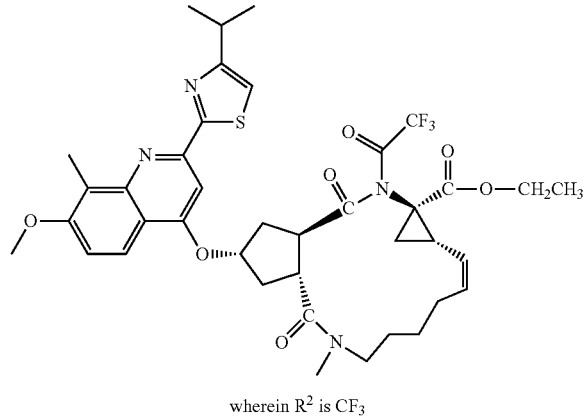

wherein $R^2$ is $CF_3$

Example 3

Path "b" Wherein $R^2$ is $CClF_2$ 3.5 mL of a solution of NQ in dichloromethane (as prepared above) and 0.17 mL (1 mmol) of chlorodifluoroacetic anhydride was added to a 0.1192 M solution of compound (1) (2.5 mL, 0.298 mmol) in dichloromethane and the resulting solution refluxed with magnetic stirring in a Radley's Caroussel tube for 1 hour 20 minutes. The solution was cooled and a $t_0$ sample was taken.

0.2 mL of a solution of 0.018 g of [1,3-bis(2,4,6-trimethylphenyl)-2-imidazolidinylidene]dichloro(3-phenyl-1H-inden-1-ylidene)-(tricyclohexyl-phosphine)-ruthenium (M2 catalyst) in 1 mL of dichloromethane was added and the resulting solution heated to reflux. A sample taken after 40 minutes contained 78% of the desired monomeric macrocycle compound (III-a), wherein $R^2$ is $CClF_2$, and no detectable amounts of compound (1) and "acylated compound (1)" (HPLC area %). The in situ yield of compound (III-a), wherein $R^2$ is $CClF_2$, determined based on the IS, was 95%.

compound (III-a)

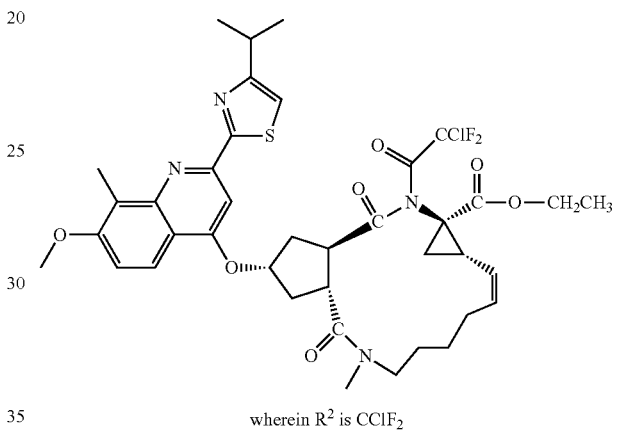

wherein $R^2$ is $CClF_2$

Example 4

Path "b" Wherein $R^2$ is $CF_3$

A solution of NQ in dichloromethane (3.5 mL) (as prepared above) and trifluoroacetic anhydride (0.14 mL, 1 mmol) was added to a 0.1192 M solution of compound (1) (2.5 mL, 0.298 mmol) in dichloromethane and the resulting solution refluxed with magnetic stirring in a Radley's Caroussel tube for 1 hour 20 minutes. The solution was cooled and a t0 sample was taken. 0.2 mL of a solution of 0.018 g of [1,3-bis(2,4,6-trimethylphenyl)-2-imidazolidinylidene] dichloro(3-phenyl-1H-inden-1-ylidene)(tricyclohexylphosphine)ruthenium (M2 catalyst) in 1 mL of dichloromethane was added and the resulting solution heated to reflux. A sample taken after 40 minutes contained 77% of the desired compound (III-a), wherein $R^2$ is $CF_3$, 2.4% of unreacted compound (1) and 0.5% of "acylated compound (1)" (HPLC area %). The in situ yield of compound (III-a), wherein $R^2$ is $CF_3$, determined based on the IS, was 94%.

compound (III-a)

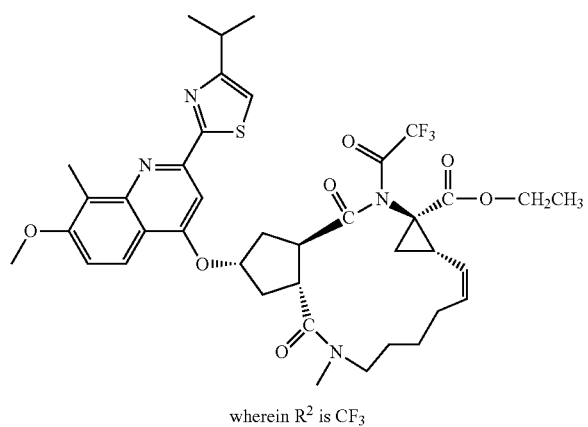

wherein R² is CF₃

Example 5a

Path "b" Wherein R² is CF₃

A 1000 mL round bottom flask, equipped with mechanical stirring, thermometer, distillation/reflux insert and nitrogen inlet, is charged with 130 mL of a 6.6 weight % solution of compound (1) in DCM (15.5 mmol). Separately, in a 1000 mL beaker, 0.2 g NQ was stirred with 450 mL of toluene for 10 minutes, the mixture filtered to give a clear yellow solution which was added to the flask. The yellow reaction mixture in the flask was stirred and heated and a solvent mixture was distilled off until the internal temperature reached 90° C. (95 mL of distillate was condensed). The mixture was cooled to 50° C. and 6.9 mL (50 mmol) of trifluoroacetic anhydride was added. The resulting solution was refluxed with stirring for 1 hour. The mixture was cooled to 40° C., 0.15 g of [1,3-bis(2, 4,6-trimethylphenyl)-2-imidazolidinylidene]dichloro(3-phenyl-1H-inden-1-ylidene)(tricyclohexylphosphine)ruthenium (M2 catalyst) was added and the resulting purple-red solution heated to 60° C. for 1 hour and 10 minutes. A sample taken after 30 minutes showed almost complete conversion of the dienes: 2.1% of unreacted compound (1), 25.7% of the desired monomeric macrocycle compound (III-a), wherein R² is CF₃, and 0.7% of "acylated compound (1)", and 4.3% of oligomeric species (HPLC area %, the rest IS and toluene). The in situ yield of the desired monomeric macrocycle compound (III-a), wherein R² is CF₃, determined based on the IS, was 67%.

compound (III-a)

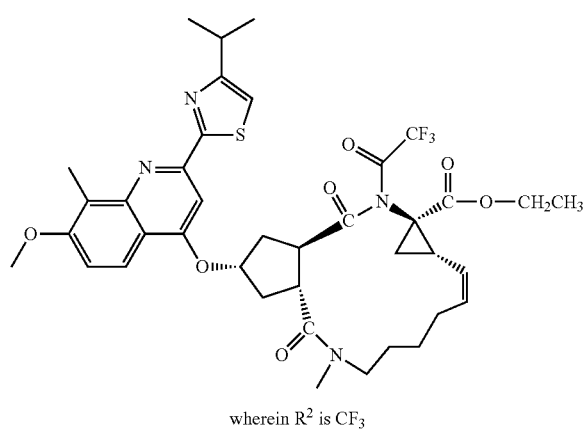

wherein R² is CF₃

Example 5b

Path "b" Wherein R² is CF₂CF₂CF₃

3.5 mL of a solution of NQ in DCM (prepared as above) and 0.24 mL (1 mmol) of perfluorobutyric anhydride was added to a 0.1192 M solution of compound (1) (2.5 mL, 0.298 mmol) in DCM and the resulting solution refluxed with magnetic stirring in a Radley's Caroussel tube for 1 hour 20 minutes. 0.2 mL of a solution of 0.018 g of [1,3-bis(2,4,6-trimethylphenyl)-2-imidazolidinylidene]dichloro(3-phenyl-1H-inden-1-ylidene)(tricyclohexylphosphine)ruthenium (M2 catalyst) in 1 mL of DCM was added and the resulting solution heated to reflux. A sample taken after 40 minutes showed the presence of 73% of the desired monomeric macrocycle T3009-COCF₂CF₂CF₃, 4% of T3008-COCF₂CF₂CF₃, and 3% of oligomeric species (HPLC-MS, UV detection area %). The in situ yield of T3009-COCF₂CF₂CF₃, determined based on the IS, was 73%.

The reaction mixture was refluxed for 3 hours 20 minutes (total cyclization reaction time 4 hours), then cooled to room temperature, 0.5 mL of ethanolamine was added and stirred for 1 hour. A sample analyzed by LC-MS showed the formation of a 2:1 mixture of the undesired macrocycle cleavage product, and the desired product.

compound (III-a)

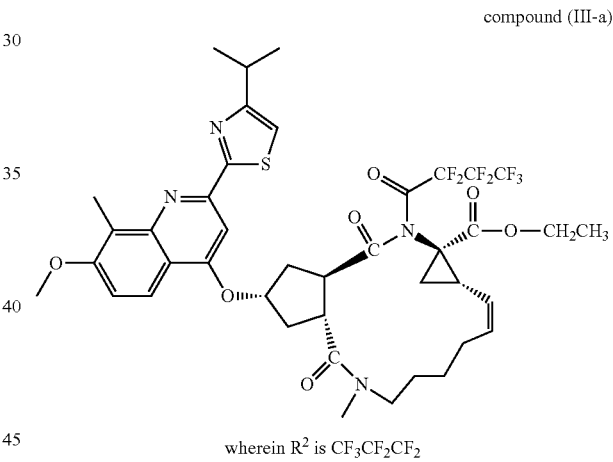

wherein R² is CF₃CF₂CF₂

Example 6

The reaction mixture of Example 4 was allowed to cool to 30° C., and 0.24 g of 2-mercaptonicotinic acid (MNA) was added, followed by the addition of 25 mL of 1-butanol, and 0.2 mL of triethylamine Analysis of this mixture after 10 minutes showed no detectable amounts of compound (2). Further 13.5 mL of triethylamine was added, and the mixture stirred overnight. Analysis of this reaction mixture showed a 12:15 mixture of the desired compound (2) and monomeric macrocycle compound (III-a), wherein R² is CF₃. The mixture was then evaporated to an oil, which was dissolved in 150 mL DCM and stirred intensively with 100 mL of water and 2.3 mL of a 40% aqueous solution of dimethylamine for 2 hours. The layers were separated, the organic layer diluted with 250 mL DCM and stirred with 6 g charcoal at room temperature for 2 hours. The mixture was filtered and evaporated to dryness to give 6.7 g of compound (2) (64% physical yield).

compound (2)

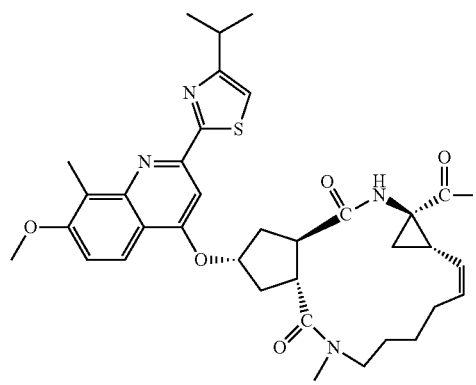

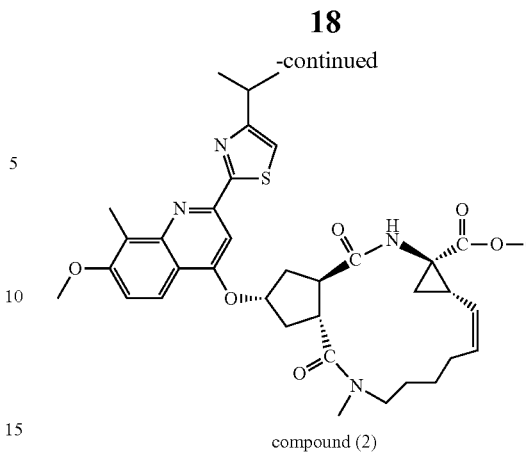

compound (2)

Examples 7, 8 and 9

The Use of (2-Methylamino)Ethanol (N-Methylethanolamine) for Acyl Cleavage Vs. The Use of Dimethylamine The starting material, compound (III-a) wherein $R^2$ is $CClF_2$, for this experiment was prepared according to Example 3.

An amount of 5 g of starting material was distributed over three 15 ml test-tubes. To the first one, 6 equivalents of dimethylamine were added. This corresponded to 345 μL of the 40 wt % aqueous solution of dimethylamine. The resulting (biphasic) solution was stirred vigorously at room temperature.

To both the other two test-tubes, 5 equivalents N-methyl ethanolamine (corresponding to 182 μL) were added and one of the resulting solutions was stirred vigorously at room temperature and the other one was heated to 40° C. in an easymax.

The reactions were monitored regularly by LC-analysis over time.

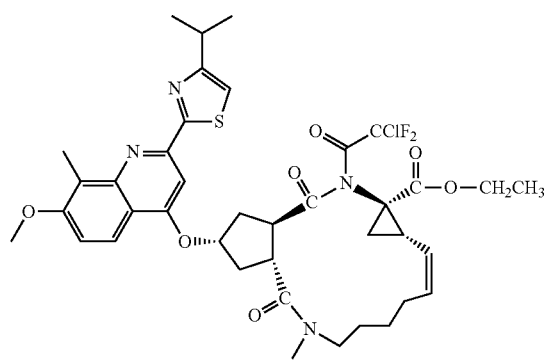

compound (III-a) wherein $R^2$ is $CClF_2$

↓ deprotection

TABLE 1 conversion of starting material (%) over time

| | Conversion of starting material (%) | | |
|---|---|---|---|
| Time (minutes) | Example 7 6 equivalents dimethylamine | Example 8 5 eq. N-methyl ethanolamine | Example 9 5 eq. N-methyl ethanolamine at 40° C. |
| 15 | 97.5 | 97.8 | 87.3 |
| 30 | 100 | 100 | 96.2 |

Example 10

Reaction of Diethyldiallylmalonate: Ring Closing Metathesis Reaction Rate Improvement by a Addition of an Iodide Compound i.e. Tetrabutyl-Ammoniumiodide In an NMR-tube, a 0.2 M solution of 700 μL $CD_2Cl_2$ and 34 μL diethyldiallylmalonate (DEDAM) (0.994 g/ml) was made. Stock solutions of M2 catalyst in DCM (665 mg in 10 ml) and tetrabutylammonium iodide (TBAI) (518 mg in 10 ml) were made and 20 μL of each stock solution (containing 1 mol % M2 and 2 mol % TBAI respectively) were added to the NMR tube.

Another reaction mixture was prepared in parallel and analogous to the one above, but instead of adding 20 μL of the TBAI stock solution, 20 μL of pure DCM was added. Both NRM tubes were left unstirred at room temperature and analyzed by NMR at certain points over a period of 24 hours. Conversions were calculated by means of the appearance and disappearance of the vinylic protons vs. the protons of the ethyl-group of the ester function and are represented vs time in the FIG. 1. From FIG. 1 it can be seen that the reaction rate and yield for the conversion of diethyldiallylmalonate (DEDAM) by the M2 catalyst is improved in the presence of the iodine compound tetrabutylammonium iodide (TBAI).

Example 11a

Reaction of Compound (1) with $(ClCF_2CO)_2O$ and M2 (Path "b"), 50 L/M Dilution, Batch, No Iodide Compound An EasyMax reactor was charged with 7 mL of a solution of compound (1) (1.99 mmol) and chlorodifluoroacetic anhydride (4 mmol) in DCM. 95.6 mL of DCM was added and the resulting yellow solution refluxed with stirring for 1 h 30 min.

2.22 mL of a DCM solution containing 28.39 mg (0.03 mmol) of [1,3-bis(2,4,6-trimethyl-phenyl)-2-imidazolidinylidene]dichloro(3-phenyl-1H-inden-1-ylidene)-(tricyclohexylphosphine)ruthenium (M2 catalyst) was added and the resulting red-brown solution heated to reflux for 4 hours. After cooling to room temperature, the reaction mixture was treated with a solution of 2-mercaptonicotinic acid (46.36 mg, 0.3 mmol) in 40% aqueous dimethylamine solution (1.26 mL, 9.96 mmol) and 5 mL water, and stirred at room temperature for 1 hour. The phases were separated, the organic phase was treated with 30 mL of DMF and was evaporated in vacuo at 60 deg C to give a DMF solution of the desired deacylated macrocycle compound (2) which was analyzed by quantitative HPLC. Yield: 79.9%.

Example 11b

Reaction of Compound (1) with $(ClCF_2CO)_2O$ and M2 (Path "b"), 50 L/M Dilution, Batch, 10 Equivalents TEAI An EasyMax reactor was charged with tetraethylammonium iodide (TEAI) (76.83 mg, 0.30 mmol), and 7 mL of a solution of compound (1) (1.99 mmol) and chlorodifluoroacetic anhydride (4 mmol) in DCM. 95.6 mL of DCM was added and the resulting brown solution refluxed with stirring for 1 hour 30 minutes. 2.22 mL of a DCM solution containing 28.39 mg (0.03 mmol) of [1,3-bis(2,4,6-trimethylphenyl)-2-imidazolidinylidene]dichloro(3-phenyl-1H-inden-1-ylidene)(tricyclohexylphosphine)-ruthenium (M2 catalyst) was added and the resulting red-brown solution heated to reflux for 4 hours. Work up was done as above. Yield: 80.2%.

TABLE 2 yield comparison of Examples 11a and 11b

| Example: | 11a | 11b |
|---|---|---|
| iodide compound: | no | 10 eq. TEAI |
| yield of compound (2) | 79.9% | 80.2% |

Example 12a

Reaction of Compound (1) with 1.2 Equivalent $(ClCF_2CO)_2O$ and M2 (Path "b"), 20 L/M Dilution, No Iodide Compound An EasyMax reactor was charged with 85 mL DCM and heated to reflux with stirring. 5 mL of a DCM solution containing 71.26 mg (0.08 mmol) of [1,3-bis(2,4,6-trimethylphenyl)-2-imidazolidinylidene]dichloro(3-phenyl-1H-inden-1-ylidene)-(tricyclohexylphosphine)ruthenium (M2 catalyst) was added. Next, of 15.1 mL of DCM solution containing 3.51 g (5 mmoles) of compound (1) and 1.05 mL (6 mmoles) of chlorodifluoroacetic anhydride was added and the mixture was stirred at reflux for 13 hours. After cooling to room temperature, the reaction mixture was treated with a solution of 2-mercaptonicotinic acid (116.38 mg) in 40% aqueous dimethylamine solution (3.17 mL) and 5 mL water, and stirred at room temperature for 1 hour. The phases were separated, and the organic phase was submitted to quantitative HPLC analysis. Yield: 76.3%.

Example 12b

Reaction of Compound (1) with 1.2 Equivalent $(ClCF_2CO)_2O$ and M2 (Path "b"), 20 L/M Dilution, 0.1 Eq. KI An EasyMax reactor was charged with 85 mL DCM and heated to reflux with stirring. 83.0 mg of potassium iodide were added and the mixture stirred for 5 minutes. 5 mL of a DCM solution containing 71.26 mg (0.08 mmol) of [1,3-bis(2,4,6-trimethylphenyl)-2-imidazolidinylidene]dichloro(3-phenyl-1H-inden-1-ylidene)-(tricyclohexylphosphine)ruthenium (M2 catalyst) was added. Next, of 14.53 mL of DCM solution containing 3.51 g (5 mmoles) of compound (1) and 1.05 mL (6 mmoles) of chlorodifluoroacetic anhydride was added via a syringe pump over 6 hours. After termination of the addition, the mixture was further stirred at reflux for 3.5 hours. After cooling to room temperature, the reaction mixture was treated with a solution of 2-mercaptonicotinic acid (116.38 mg) in 40% aqueous dimethylamine solution (3.17 mL) and 5 mL water, and stirred at room temperature for 1 hour. The phases were separated, and the organic phase was submitted to quantitative HPLC analysis. Yield: 86.6%.

TABLE 3 yield comparison of Examples 12a and 12b

| Example: | 12a | 12b |
|---|---|---|
| iodide compound: | no | 0.1 eq. KI |
| yield of compound (2) | 76.3% | 86.6% |

Example 13a

Reaction of Compound (1) with 1.2 Equivalent $(ClCF_2CO)_2O$ and M2 (Path "b"), 20 L/M Dilution, No Iodide Compound A catalyst stock solution was prepared by dissolving 113 mg of [1,3-bis(2,4,6-trimethylphenyl)-2-imidazolidinylidene]dichloro(3-phenyl-1H-inden-1-ylidene)-(tricyclohexylphosphine)ruthenium (M2 catalyst) in 8 mL DCM at room temperature. An EasyMax reactor was charged with 85 mL DCM and heated to reflux with stirring. 1.67 mL of the above catalyst stock solution was added to the reactor and the mixture stirred at reflux for 5 minutes. Using two separate syringe pumps, addition of the two solutions was started at the same time: 3.33 mL of the above catalyst stock solution were added over 6 hours 15 minutes and 13.87 mL of a DCM solution containing 3.51 g (5 mmoles) of compound (1) and 1.05 mL (6 mmoles) of chlorodifluoroacetic anhydride were added over 6 hours. After termination of the addition, the mixture was further stirred at reflux for 3.5 hours. After cooling to room temperature, the reaction mixture was treated with a solution of 2-mercaptonicotinic acid (116.38 mg) in 40% aqueous dimethylamine solution (3.17 mL) and 5 mL water, and stirred at room temperature for 1 hour. The phases were separated, and the organic phase was submitted to quantitative HPLC analysis. Yield: 80.6%.

Example 13b

Reaction of Compound (1) with 1.2 Equivalent (ClCF$_2$CO)$_2$O and M2 (Path "b"), 20 L/M Dilution, 0.1 Equivalent TBAI A catalyst stock solution was prepared by dissolving 114 mg of [1,3-bis(2,4,6-trimethylphenyl)-2-imidazolidinylidene]dichloro(3-phenyl-1H-inden-1-ylidene)-(tricyclohexylphosphine)ruthenium (M2 catalyst) and 297 mg tetrabutylammonium iodide in 8 mL DCM at room temperature.

An EasyMax reactor was charged with 85 mL DCM and heated to reflux with stirring. 1.67 mL of the above catalyst stock solution was added to the reactor and the mixture stirred at reflux for 5 minutes. Using two separate syringe pumps, addition of the two solutions was started at the same time: 3.33 mL of the above catalyst stock solution were added over 6 hours 15 minutes and 13.87 mL of a DCM solution containing 3.51 g (5 mmoles) of compound (1) and 1.05 mL (6 mmoles) of chlorodifluoroacetic anhydride were added over 6 hours. After termination of the addition, the mixture was further stirred at reflux for 3.5 hours. After cooling to room temperature, the reaction mixture was treated with a solution of 2-mercaptonicotinic acid (116.38 mg) in 40% aqueous dimethylamine solution (3.17 mL) and 5 mL water, and stirred at room temperature for 1 hour. The phases were separated, and the organic phase was submitted to quantitative HPLC analysis. Yield: 86.4%.

Example 13c

Reaction of Compound (1) with 1.2 Equivalent (ClCF$_2$CO)$_2$O and M2 (Path "b"), 20 L/M Dilution, 0.1 Eq. TEAI A catalyst stock solution was prepared by mixing 124 mg of [1,3-bis(2,4,6-trimethylphenyl)-2-imidazolidinylidene]dichloro(3-phenyl-1H-inden-1-ylidene)-(tricyclohexylphosphine)ruthenium (M2 catalyst) and 173 mg tetraethylammonium iodide in 6.7 mL DCM at room temperature The tetraethylammonium iodide did not completely dissolve—the supernatant, i.e. the solution phase of this mixture was used. An EasyMax reactor was charged with 85 mL DCM and heated to reflux with stirring. 1.67 mL of the above catalyst stock solution was added to the reactor and the mixture stirred at reflux for 5 minutes. Using two separate syringe pumps, addition of the two solutions was started at the same time: 3.33 mL of the above catalyst stock solution were added over 3 hours 15 minutes and 13.87 mL of a DCM solution containing 3.51 g (5 mmoles) of compound (1) and 1.05 mL (6 mmoles) of chlorodifluoroacetic anhydride were added over 3 hours. After termination of the addition, the mixture was further stirred at reflux for 3 hours. After cooling to room temperature, the reaction mixture was treated with a solution of 2-mercaptonicotinic acid (116.38 mg) in 40% aqueous dimethylamine solution (3.17 mL) and 5 mL water, and stirred at room temperature for 1 hour. The phases were separated, and the organic phase was submitted to quantitative HPLC analysis. Yield: 89.3%.

TABLE 4 yield comparison of Examples 13a to 13c

| Example: | 13a | 13b | 13c |
|---|---|---|---|
| iodide compound: | no | 0.1 eq. TBAI | 0.1 eq. TEAI |
| yield of compound (2) | 80.6% | 86.4% | 89.3% |

Example 14

Reaction of Compound (1) with 2.0 Equivalent (ClCF$_2$CO)$_2$O and M2 (Path "b"), 50 L/M Dilution, 0.15 Eq. TEAI A catalyst stock solution was prepared by mixing 1.03 g of [1,3-bis(2,4,6-trimethylphenyl)-2-imidazolidinylidene]dichloro(3-phenyl-1H-inden-1-ylidene)-(tricyclohexylphosphine)ruthenium (M2 catalyst) and 100.82 mL DCM at room temperature under nitrogen in an EasyMax reactor.

A stock solution of the acylated diene was prepared in a 250 mL 4-neck round bottom flask by mixing 148.85 mL of DCM solution containing 72.014 mmoles of compound (1), 57.61 mL DCM and 25.12 mL of chlorodifluoroacetic anhydride. The mixture was stirred at room temperature for 30 minutes, and diluted to an end volume of 200 mL. In a 5 L round bottom flask equipped with mechanical stirring, reflux condenser, thermometer and inlet for the addition cannulae, 2.78 g of tetraethylammonium iodide were mixed with 3.36 L of DCM. The mixture was then heated to reflux with stirring. From a syringe pump, 100 mL of the above catalyst stock solution were added over 2 hours 30 minutes. From a second syringe pump, 200 mL of the stock solution of the acylated diene was added over 2 hours (addition from the second syringe pump was started 15 minutes after the start of the first syringe pump). After termination of the addition, the mixture was further stirred at reflux for 10 hours. After cooling to room temperature, the reaction mixture was treated with a solution of 2-mercaptonicotinic acid (1.68 g) in 40% aqueous dimethylamine solution (3.17 mL), and stirred at room temperature for 2 hours. 540.10 mL of water were added, the stirring was stopped and the phases were separated. The organic layer was washed with 410.48 mL of water, separated, evaporated to a total volume of 274.11 mL and transferred to a 500 ml 4-neck RBF for the crystallization procedure.

The mixture was further evaporated while 2-butanone was gradually added to reach an internal temperature of 79.6° C. (total 2-butanone volume 279.83 mL). The mixture was cooled to 75° C., seeded and allowed to cool. The precipitate was filtered, washed consecutively with 28.81 mL of 2-butanone and with 2 portions of 28.81 mL of EtOH. The filter cake was dried at 60° C. for 71.75 hours to give 33.88 g of product compound (2), 69.71% isolated yield. Physical and chemical characterization data of this compound were consistent with the data reported in WO-2007/014926 in Example 4 Step E on page 74.

DESCRIPTION OF THE DRAWINGS

FIG. 1: conversion of diethyldiallylmalonate (DEDAM) by M2 catalyst in the presence and absence of tetrabutylammonium iodide (TBAI).

The invention claimed is:
1. A process for preparing a compound with the following formula:

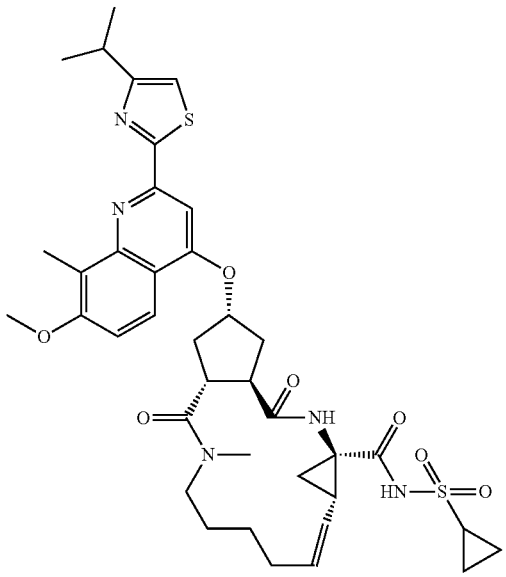 [SMILES: COc1ccc2c(O[C@@H]3C[C@H]4C(=O)N[C@]5(C(=O)NS(=O)(=O)C6CC6)C[C@H]5/C=C/CCCCN(C)C(=O)[C@@H]4C3)cc(-c3nc(C(C)C)cs3)nc2c1C]

comprising
a) acylating a diene compound of formula (I), wherein $R^1$ is $C_{1-6}$alkyl, compound (I)

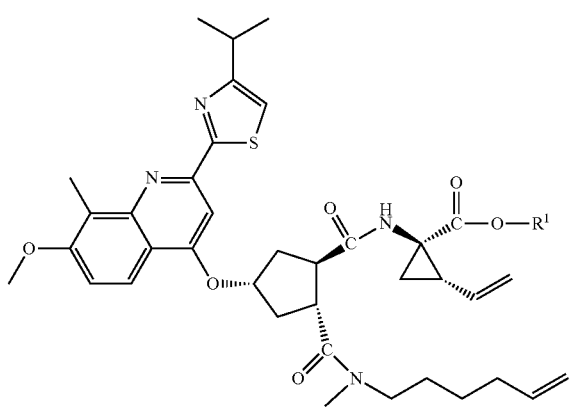

with a halogenated acyl compound $(R^2\text{—CO})_2O$ or $R^2\text{—COCl}$, wherein $R^2$ is polyhalo$C_{1-4}$alkyl, followed by a ring-closing metathesis reaction of the acylated reaction product with a suitable catalyst in a reaction-inert solvent to yield a compound of formula (III); and compound (III)

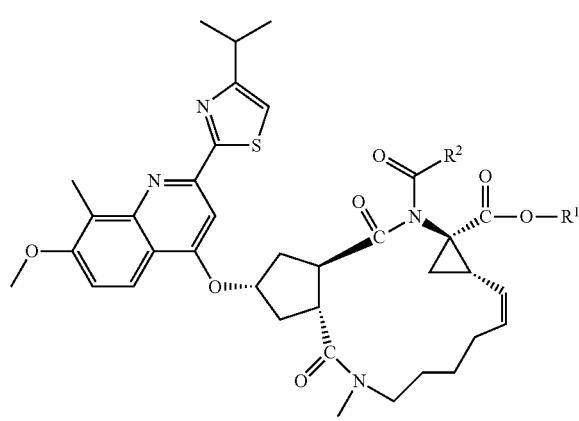

b) removing the halogenated acyl group from compound (III) thus obtaining the compound of formula (II)

compound (II)

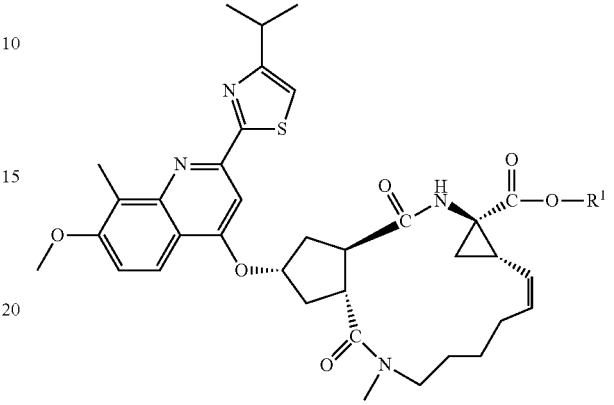

wherein $R^1$ is $C_{1-6}$alkyl; and c) reacting the compound of formula (II) with cyclopropylsulfonamide.

2. The process according to claim 1 wherein $R^1$ represents $C_{1-4}$alkyl.

3. The process according to claim 2 wherein $R^1$ represents ethyl.

4. The process according to claim 1 wherein the halogenated acyl compound is $(R^2\text{—CO})_2O$.

5. The process according to claim 4 wherein $R^2$ represents trifluoromethyl, chloro-difluoromethyl, or heptafluoropropyl.

6. The process according to claim 5 wherein $R^2$ represents chlorodifluoromethyl.

7. The process according to claim 1 wherein the suitable catalyst in the ring closing metathesis reaction is selected from the group consisting of [1,3-bis(2,4,6-trimethyl-phenyl)2imidazolidinylidene]dichloro(phenylmethylene) (tricyclohexylphosphine) ruthenium, [1,3-bis(2,4,6-trimethylphenyl)-2-imidazolidinylidene]dichloro[[2-(1-methylethoxy-κO)phenyl]methylene-κC], dichloro(3-phenyl-1H-inden-1-ylidene)bis(tricyclohexylphosphine)ruthenium or bis(tricyclohexyl-phosphine) [(phenylthio)methylene] ruthenium dichloride, dichloro(phenylmethylene)bis(tricyclohexylphosphine)ruthenium, dichloro[[2-(1- methylethoxy-α-O)phenyl]methylene-α-C](tricyclohexylphosphine) ruthenium, [1,3-bis(2,4,6-trimethylphenyl)-2-imidazolidinylidene]dichloro(3-phenyl-1H-inden-1-ylidene) (tricyclohexylphosphine)ruthenium, [1,3-bis(2,4,6-trimethylphenyl)-2-imidazolidinylidene]dichloro(3-phenyl-1H-inden-1-ylidene)(triphenylphosphine) ruthenium and [1,3-bis(2,4,6-trimethylphenyl)-2-imidazolidinylidene] dichloro[[4-[(dimethylamino)sulfonyl]-2-(1-methylethoxy-κO)phenyl]methyl-κC]ruthenium.

8. The process according claim 7 wherein the suitable catalyst in the ring closing metathesis reaction is [1,3-bis(2,4,6-trimethylphenyl)-2-imidazolidinylidene]dichloro(3-phenyl-1H-inden-1-ylidene)(tricyclohexylphosphine)ruthenium.

9. The process according to claim 1 wherein the ring closing metathesis reaction is carried out in the presence of reaction solvent soluble tetraalkylammonium iodide selected from tetramethylammonium iodide (TMAI), tetraethylammonium iodide (TEAI), tetrapropylammonium iodide (TPAI), or tetrabutylammonium iodide (TBAI).

10. The process according to claim 1 wherein the removal of the halogenated acyl group is carried out by treatment with a secondary amine, in particular dimethylamine.

11. The process according to claim 1 wherein steps a) and b) are carried out in a one-pot reaction.

* * * * *